United States Patent [19]

Richardson et al.

[11] Patent Number: 5,219,750
[45] Date of Patent: Jun. 15, 1993

[54] PRODUCTION OF CYANIDE HYDRATASE

[75] Inventors: Kenneth R. Richardson, Middlesbrough; Peter M. Clarke, Nottingham, both of England

[73] Assignee: Imperial Chemical Industries PLC, London, England

[21] Appl. No.: 885,255

[22] Filed: May 20, 1992

Related U.S. Application Data

[63] Continuation of Ser. No. 681,470, Apr. 4, 1991, abandoned, which is a continuation of Ser. No. 406,861, Sep. 11, 1989, abandoned, which is a continuation of Ser. No. 16,002, Feb. 18, 1987, abandoned.

[30] Foreign Application Priority Data

Feb. 19, 1986 [GB] United Kingdom ............. 8604068

[51] Int. Cl.$^5$ ............. C12N 9/88; C02F 3/34
[52] U.S. Cl. ............. 435/232; 435/245; 435/262.5; 435/813; 435/821; 210/606; 210/632
[58] Field of Search ......... 435/232, 262, 262.5, 435/243, 813, 929, 821; 210/606, 611, 632

[56] References Cited

U.S. PATENT DOCUMENTS

| | | | |
|---|---|---|---|
| 4,048,017 | 9/1977 | Roesler | 435/813 UX |
| 4,402,831 | 9/1983 | Beardsmore et al. | 210/606 |
| 4,440,644 | 4/1984 | Mudder et al. | 210/611 |
| 4,511,657 | 4/1985 | Colarotolo et al. | 435/253 |

FOREIGN PATENT DOCUMENTS

| | | |
|---|---|---|
| 0061249 | 9/1982 | European Pat. Off. |
| 116423 | 8/1984 | European Pat. Off. |
| 0233719 | 8/1987 | European Pat. Off. |
| 2027685 | 2/1980 | United Kingdom |

OTHER PUBLICATIONS

Bio/Technology vol. 3, Jul. 1985, p. 601.
Microbial Technology, Microbial Processes, vol. 1, H. J. Peppler and D. Perlman, 2nd Edition, Academic Press, Inc., pp. 288–297 (1979).
Japanese J. Ferment Technol., vol. 45, No. 7, pp. 630–636 (1967).
Japanese J. Ferment Technol., vol. 46, No. 10, pp. 807–813 (1968).
Japanese J. Ferment Technol., vol. 47, No. 10, pp. 639–643 (1969).
Japanese J. Ferment Technol., vol. 47, No. 10, pp. 644–650 (1969).
Japanese J. Ferment Technol., vol. 48, No. 5, pp. 277–282 (1970).
Japanese J. Ferment Technol., vol. 48, No. 5, pp. 285–290 (1970).
Archives of Biochem & Biophys., 151, pp. 468–474 (1972).
Phytopathology, 67, pp. 1001–1006 (1977).
Millar in Chemical Abstracts vol. 77 84953p (1972).
Nazly et al in Chemical Abstracts vol. 95 155901e (1981).
Fry, W. E., et al. (1972) Arch. Biochem, Biophys, 151, 468–474.

Primary Examiner—Charles L. Patterson, Jr.
Attorney, Agent, or Firm—Cushman, Darby & Cushman

[57] ABSTRACT

A process for the production of the enzyme cyanide hydratase which comprises continuously cultivating a microorganism strain under specified conditions of temperature, pH and dilution rate whilst continuously supplying cyanide ions and/or hydrogen cyanide and/or compounds which generate cyanide ions and/or hydrogen cyanide under fermentation conditions to the culture. A method for the treatment of a cyanide-containing material to degrade the cyanide therein which uses cyanide hydratase produced by the process of the invention is also claimed. Preferably the microorganism is a Fusarium strain, in particular *Fusarium lateritium* Naas CM1 300533 deposited at The Commonwealth Mycological Institute, Kew, Richmond Surrey, England under the terms of the Budapest Treaty.

10 Claims, 1 Drawing Sheet

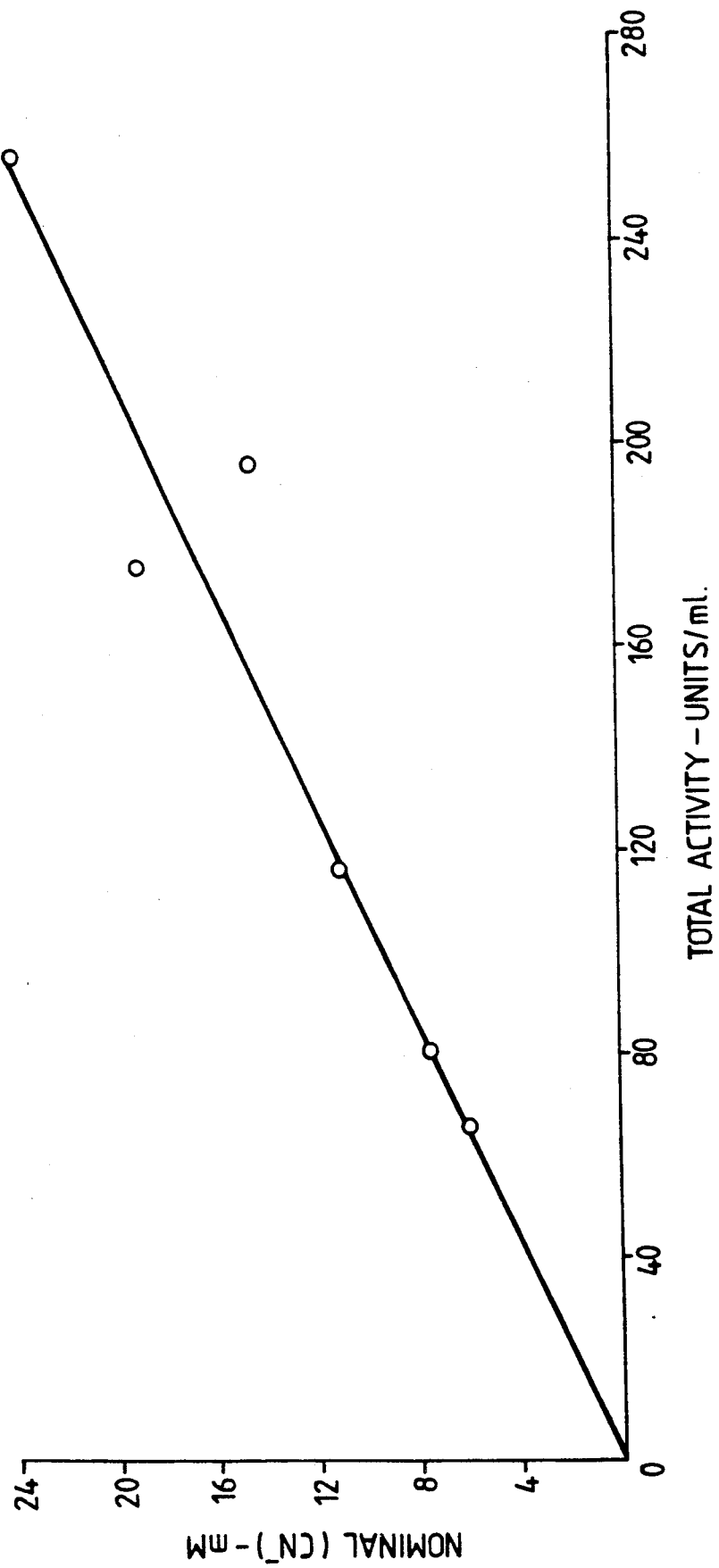

PRODUCTION OF CYANIDE HYDRATASE

This is a continuation of Application Ser. No. 07/681,470, filed on Apr. 4, 1991, which was abandoned upon the filing hereof which is a continuation of Ser. No. 07/406,861, filed Sep. 11, 1989, now abandoned and which is a continuation of Ser. No. 07/016,002, filed Feb. 18, 1987, now abandoned.

This invention relates to a process for the production of cyanide hydratase.

Certain fungi contain the enzyme cyanide hydratase EC No. 4.2.1.66 (otherwise known as formamide hydrolyase) which is capable of degrading cyanide to formamide (see for example Archives of Biochemistry and Biophysics, 151, pages 468 to 474, (1972) and Phytopathology, 67, pages 1001 to 1006, (1977)) and the following references from the Japanese J. Ferment. Technol.: Vol. 45, No. 7, p 630–636 (1967); Vol. 46, No. 10, p 807–813 (1968); Vol. 47, No. 10, p 639–643 and 644–650 (1969) and Vol. 48, No. 5, p 277–282 and 285–290 (1970). It has been proposed to use such fungi in the microbiological treatment of cyanide containing effluents (see for example our European Patent No. 61249). To be suitable for this purpose it is desirable that the fungi contain a cyanide hydratase enzyme which is stable over a significant period of time and has a high level of activity.

According to the present invention we provide a process for the production of the enzyme cyanide hydratase which comprises the steps of (A) continuously cultivating a microorganism strain aerobically in an aqueous culture containing sources of carbon and of appropriate inorganic nutrients at a temperature within the range 28° to 34° C., a pH in the range 4.5 to 7.5 and a dilution rate not greater than $0.11\ hr^{-1}$ whilst continuously supplying cyanide ions and/or hydrogen cyanide and/or compounds which generate cyanide ions and/or hydrogen cyanide under fermentation conditions to the culture at a concentration equivalent to at least 15 mM (cyanide ion and/or hydrogen cyanide in the total medium, supplied to the culture) and (B) recovering cells containing cyanide hydratase from the culture.

A method for the treatment of a cyanide-containing material to degrade the cyanide therein in which the material is treated with cyanide hydratase or a composition comprising cyanide hydratase characterized in that the cyanide hydratase has been produced by the process of the invention is also included in the scope of the invention.

The cyanide ions added to the culture become hydrogen cyanide under the conditions of the culture.

Preferably the microorganism strain is a fungal strain although suitable bacterial strains may also be used. Fungi that may be used in the process of the invention include *Stemphylium loti*, e.g. ATCC 11718; *Mycoleptodiscus terrestris*, e.g. CBS 231.53; *Fusarium moniliforme*, e.g. No. 3104.SA.49a available from the Canadian Department of Agriculture, Culture Collection, Ottawa, and which has also been deposited as CBS 161.82; *Helminthosporium sorghicola*, otherwise known as *Drechslera sorghicola*, e.g. CBS 249.49; *Periconia circinata*, e.g. CBS 263.37; and *Glomerella tucamanensis*, CBS 132.37. (ATCC No. refers to the number designated by the American Type Culture Collection, 12301 Park Lawn Drive, Rockville, Md. 20852, USA, while CBS No. refers to the number designated by the Central Bureau Voor Schimmelcultures, Baarn, Netherlands).

Other fungi that may be used and which have been described in the literature as producing the enzyme include *Collectotrichum graminicola, Gloeocercospora sorghi, Helminthosphorium turcicum, H. maydis, H. carbonum, H. victoriae*, and *H. Phomna*.

Preferred fungal strains are Fusarium strains, particularly *Fusarium lateritium* Nees strain CMI 300533, deposited Feb. 3, 1986 at the Commonwealth Mycological Institute, Ferry Lane, Kew, Richmond, Surrey, TW9 3AF, England; and variants and mutants derived therefrom. Preferred fungal strain CMI 300533 is non-pathogenic to wheat and has the following morphological characteristics:

Media (1) Potato Glucose Agar (PSA)

250 grams of potatoes washed and diced, placed in pressure cooker at 15 lbs./square inch for 15 minutes. The decoction is then squeezed through two layers of muslin, 2% of Glucose and 2% of Agar are added to the turbid filtrate and the medium autoclaved and dispersed.

(2) Czapek-Dox (Modified) Agar (Oxoid) (CDA) "Oxoid" is a Registered Trade Mark

Growth conditions: 25° C., several weeks

Rate of growth: 4.0 cm. in 3 days, 3.0 cm, in 3 days respectively

Character of growth: Floccose, spreading colonies with white aerial mycelium. Substratum on PSA greyish rose with patches of crimson to yellow. Tendency to be somewhat paler on CDA. Occasionally deep red pigment produced, particularly on aging. After one to two weeks the aerial mycelium tends to become brown and collapse. The colony then becomes rather slimy as sporodochia are formed the colour being pink to brown on PSA and salmon pink on CDA.

No exudate is formed and pigment formation tends to follow the mycelium colour.

Conidia: Microconidia not produced by this organism. Macroconidia produced from single lateral phialides or multibranched conidiophores with short phialides. In older cultures the conidiophores aggregate to form sporodochia, particularly on CDA. The conidia vary from falcate to curved fusoid dorsi-ventral, septation varying from 3 to 5, commonly 5 in younger cultures. Spore size varies from $25-50\mu \times 2.5\mu - 4.0\mu$.

The foot cell is often pedicellate, particularly in the longer 5 septate spores. Swollen cells occur in the mycelium and occasionally chlamydospores occur intercalary, singly or in chains.

A process for the production of the enzyme cyanide hydratase by aerobically cultivating cells of *Fusarium lateritium* Nees CMI 300533 is described and claimed in our co-pending UK Patent applications Nos. 8604069 and 8607595.

Fungi can be made to grow in two distinct forms, namely a ball or pellet form or in a dispersed form where the fungal cells are diffuse filamentous strands dispersed in the growth medium. For use in effluent treatment it is important that the fungus is grown in the dispersed, as opposed to ball or pellet, form. As growth in the pellet form is hampered by diffusion of nutrients and gases through the pellet, this makes cultivation inefficient. The conditions of the cultivation step (A) of the process of the invention are such as to encourage growth in the dispersed form.

In the cultivation step (A) of the process the fungal strain may suitably be grown under conditions of carbon or oxygen limitation. Preferably however the conditions are such that growth takes place effectively under dual carbon and oxygen limitation. Preferably the culture medium is a defined medium, i.e. one containing only mineral salts in addition to the carbon source without any undefined organic materials such as yeast extract.

Any suitable carbon source may be used in the process but glucose is preferred. Preferred sources of nitrogen include ammonium sulphate and ammonium hydroxide and preferred sources of phosphorus include potassium phosphate and phosphoric acid. Preferably the main constituents of the culture medium are present in the medium supplied to the process during its steady state in concentrations within the following ranges:

| | | |
|---|---|---|
| $H_3PO_4$ | 10–20 | mM |
| $K_2SO_4$ | 800–1400 | ppm |
| $MgSO_4.7H_2O$ | 700–1200 | ppm |
| $Glucose.1H_2O$ | 10,000–40,000 | ppm |
| $(NH_4)_2SO_4$ | 500–3000 | ppm |
| Trace nutrients | 0.1 ppm–20 ppm | |

A very suitable culture medium to be supplied to the culture during steady state conditions has the following constitution:

| | |
|---|---|
| 1.1M $H_3PO_4$ | 320 ml/20 L |
| Trace metals/Biotin | 10 ml/20 L |
| $K_2SO_4$ | 20 g/20 L |
| $MgSO_4.7H_2O$ | 18 g/20 L |
| $Glucose.1H_2O$ | 223 g/20 L |
| $(NH_4)_2SO_4$ | 50 g/20 L |

Trace metals/Biotin (per liter)

| | |
|---|---|
| $FeCl_3.6H_2O$ | 9.6 g |
| $CuSO_4.5H_2O$ | 3.6 g |
| $MnSO_4.4H_2O$ | 30.0 g |
| $ZnSO_4.7H_2O$ | 38.0 g |
| Biotin | 0.52 g |

Cyanide ions or hydrogen cyanide are supplied to the culture either separately or together with other nutrients throughout the cultivation step of the process. Preferably cyanide is added to the medium supplied to the process as alkali metal cyanides such as sodium or potassium cyanide. During start-up of the cultivation step cyanide is added initially in a low concentration which is gradually increased as the tolerance of the fungal cells in the culture towards it increases. Finally during steady state cultivation cyanide is supplied at a concentration of at least 15 mM, in the total medium supplied to the culture; i.e. the sum of all the liquid feeds to the culture, preferably 2–10 (especially 4–6) m mole/g dry cell weight. We have found that higher concentrations of cyanide ions in the medium supplied to the culture during its steady state lead to increased activity of the cyanide hydratase enzyme in the cells and that the level of enzyme activity increases linearly with increases in the cyanide ion concentration. For example enzyme activity in units of $\mu$ mole formamide produced per minute per ml of culture at a low level (5 mM) of cyanide addition is 55 whereas the enzyme activity at a higher level (20 mM) is 220 units.

Preferred conditions for the cultivation step (A) of the process are as follows: dilution rate in the range 0.05 to 0.1 $hr^{-1}$; pH in the range 5.0 to 6.0, especially 5.5; and temperature in the range 28° to 32° C., especially 30° to 32° C. for highest enzyme activity.

During the cultivation step, culture is continuously removed from the fermenter in which cultivation takes place and cells containing the enzyme cyanide hydratase are separated from the removed culture by any suitable means, filtration being preferred. The separated cells may then be dried and further treated, e.g. by extrusion, to produce cyanide hydratase-containing cellular material in any suitable form, e.g. in aggregates or as a powder. Whilst the enzyme could be separated from the cells and used in cell-free form, this is generally not necessary and the enzyme is usually not separated from the cells containing it. The fungal mycelia containing the cyanide hydratase can be immobilized as described in our European Patent No. 61249 but again this refinement is generally not carried out.

The cyanide hydratase material produced by the process of the invention is very suitable for the treatment of cyanide-containing aqueous effluents, e.g. by the process of our European Patent No. 61249. The enzyme produced has a high shelf-life stability (for example half life of up to 130 days) and a high activity. Enzyme-containing material having particularly high stability is produced when the cultivation step of the process is operated under conditions of oxygen limitation or of dual oxygen and carbon limitation. Enzyme-containing material having particularly high activity is produced when the cultivation step of the process is carried out at a temperature in the range 30° to 32° C.

The invention is illustrated by the following Examples:

EXAMPLE 1

Cyanide hydratase activity was induced by growing Fusarium strain CMI 300533 in the presence of HCN in continuous culture on a glucose limiting, defined medium. Steady states were set up at different culture temperatures at a pH of 5.5 and a dilution rate of 0.10 $h^{-1}$. The results are set out in Table 1. This shows that maximal enzyme activity was induced at 30° C.–32° C. and that growth below this temperature halved the induced activity. Growth at 34° C. resulted in wash-out of the culture. Enzyme activity units are $\mu$ mols of formamide produced per minute from 100 mM sodium cyanide at pH 8.5

TABLE 1

| Effect of temperature on activity | | | |
|---|---|---|---|
| pH | Sp. act. (units/mg dry weight) | Dil. rate ($h^{-1}$) | Temp (°C.) | [CN] (mM) |
| 5.5 | 59.3 | 0.05 | 30.0 | 15.4 |
| 5.5 | 27.5 | 0.05 | 28.0 | 14.4 |
| 5.5 | 27.1 | 0.05 | 27.0 | 15.2 |
| 5.5 | 25.5 | 0.05 | 25.0 | 13.2 |
| 5.5 | 22.7 | 0.05 | 25.0 | 14.7 |
| 5.5 | 52.4 | 0.05 | 30.0 | 14.0 |
| 5.5 | 52.3 | 0.05 | 32.0 | 14.8 |

EXAMPLE 2

Levels of cyanide hydratase were induced by growing Fusarium strain CMI 300533 in the presence of HCN in continuous culture on a glucose limited, defined, medium. Steady states were set up at various oxygenation rates with pH (5.5), temperature (30° C.) and dilution rate (0.10 $h^{-1}$) remaining constant. The induced enzyme was freeze dried and stored at 4° C.

over silica gel and the stability of the enzyme preparations monitored by assaying aliquots of the preparations over time. The results are set out in Table 2. This shows that stability of the enzyme in storage increased when the culture was grown under dual oxygen/carbon limitation.

TABLE 2

| Oxygenation | 1st half-life |
| --- | --- |
| Aerobic | 21 days |
| mild anoxia | 63 days |
| severe anoxia | 90 days |

EXAMPLE 3

The induction profile of cyanide hydratase was determined by growing Fusarium strain CMI 300533 in continuous culture on a glucose limited, defined, medium. Steady states were set up at various influent HCN concentrations with pH (5.5), temperature (30° C.) and dilution rate (0.10 h$^{-1}$) remaining constant.

The graph shown in the drawing shows a linear response between levels of induced activity and cyanide concentration up to (at least) 24 mM cyanide in the influent medium. In the graph nominal cyanide concentration in millimolar units is plotted as ordinate with total activity (as defined above) as abscissa.

EXAMPLE 4

Fusarium strain CMI 300533 was grown continuously in a 6000 l volume vessel using a defined medium containing glucose as carbon source, the glucose concentration being growth limiting. The pH was between 5.0 and 5.8, the dilution rate was 0.08 to 0.1 hr$^{-1}$ and the temperature was 30° to 32° C. Sodium cyanide was added to the nutrient feed at a concentration between 61.5 and 73.5 mM. The culture was subjected to oxygen stress by reduction of the aeration rate which resulted in the production of up to 0.81 g ethanol/l. Over a period of 140 hours biomass was produced at between 12.2 and 14.3 g/l with a cyanide hydratase activity of 81.0 to 122.4 µ moles formamide produced per minute per mg dry weight (assayed using 120 mM solutions of cyanide at pH 8.5 and 20° C.).

We claim:

1. A process for the production of the enzyme cyanide hydratase of increased activity and stability which comprises the steps of (A) continuously cultivating a microorganism strain aerobically in an aqueous culture containing sources of carbon and of appropriate inorganic nutrients at a temperature in the range 28° to 34° C., a pH in the range 4.5 to 7.5 and a dilution rate not greater than 0.11 hr$^{-1}$ while continuously supplying throughout the cultivation at least one member of the group consisting of cyanide ions, hydrogen cyanide, sources of cyanide ions and sources of hydrogen cyanide to the culture, said member being added initially at a low concentration which is gradually increased as cell tolerance to the cyanide ions or hydrogen cyanide increases so that when steady state cultivation is reached, said member is supplied continuously to completion of the cultivation at a concentration equivalent to at least 15 mM of said member in the total medium supplied to the culture, and (B) then recovering cells containing cyanide hydratase of increased activity and stability from the culture.

2. A process according to claim 1 characterized in that the microorganism strain is a strain of the genus Fusarium.

3. A process according to claim 2 characterized in that the strain is *Fusarium lateritium* Nees strain CMI 300533 or a variant or mutant derived therefrom.

4. A process according to claim 1 wherein in the cultivation step (A) the microorganism strain is cultivated under conditions selected from the group consisting of carbon limitation, oxygen limitation and dual carbon and oxygen limitation.

5. A process according to claim 1 wherein the carbon source is glucose.

6. A process according to claim 1 wherein said at least one member is supplied to the culture at a concentration in the total medium in a range equivalent to 2–10 m mole/g dry cell weight.

7. A process according to claim 6 wherein said at least one member is supplied to the culture at a concentration in the total medium in a range equivalent to 4–6 m mole/g dry cell weight.

8. A process according to claim 1 wherein the pH is in the range 5.0 to 6.0.

9. A process according to claim 1 wherein the temperature is in the range 30° to 32° C.

10. The process of claim 1 wherein the microorganism strain is selected from the group consisting of *Stemphylium loti, Mycoleptodiscus terrestris, Fusarium moniliforme, Helminthosporium sorghicola, Periconia circinata, Glomereella tucamanensis, Collectotrichum graminicola, Gloeocercospora sorghi, Helminthosphorium turcicum, H. maydis, H. carbonum, H. phomna*, and Fusarium strains.

* * * * *